(12) United States Patent
Mann et al.

(10) Patent No.: US 9,131,696 B2
(45) Date of Patent: Sep. 15, 2015

(54) HERBICIDAL COMPOSITIONS COMPRISING FLUROXYPYR AND FLUMETSULAM

(71) Applicant: Dow AgroSciences LLC, Indianapolis, IN (US)

(72) Inventors: Richard K. Mann, Franklin, IN (US); Andrea C. McVeigh-Nelson, Indianapolis, IN (US); Amy Gwinn, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/135,048

(22) Filed: Dec. 19, 2013

(65) Prior Publication Data
US 2014/0179525 A1    Jun. 26, 2014

Related U.S. Application Data

(60) Provisional application No. 61/740,248, filed on Dec. 20, 2012.

(51) Int. Cl.
*A01N 43/60* (2006.01)
*A01N 43/90* (2006.01)

(52) U.S. Cl.
CPC ..................... *A01N 43/90* (2013.01)

(58) Field of Classification Search
None
See application file for complete search history.

(56) References Cited

U.S. PATENT DOCUMENTS 6,294,503 B1 * 9/2001 Gupta et al. ............... 504/225

FOREIGN PATENT DOCUMENTS

CN    102283220    * 12/2011

* cited by examiner

*Primary Examiner* — Alton Pryor
(74) *Attorney, Agent, or Firm* — Michael J. Terapane; Meunier Carlin & Curfman, LLC

(57) ABSTRACT

Herbicidal compositions containing (a) fluoroxypyr or an agriculturally acceptable salt or ester thereof and (b) flumetsulam or an agriculturally acceptable salt thereof provide synergistic herbicidal control of undesirable vegetation, e.g., in wheat, barley, oats, rye, sugarcane, rice, sorghum, corn/maize, soybean, rice, sunflower, canola/oilseed rape, sugarcane, sorghum, cotton, pastures, grasslands, rangelands, fallowland, turf, tree and vine orchards, industrial vegetation management and rights-of-way; or crops comprising an aad-12 gene. Also provided herein are methods of using herbicidal compositions containing (a) fluroxypyr or an agriculturally acceptable salt or ester thereof and (b) flumetsulam or an agriculturally acceptable salt thereof.

32 Claims, No Drawings

HERBICIDAL COMPOSITIONS COMPRISING FLUROXYPYR AND FLUMETSULAM

CROSS REFERENCE TO RELATED APPLICATIONS

This application claims the benefit of U.S. Provisional Patent Application Ser. No. 61/740,248, filed Dec. 20, 2012, the disclosure of which is expressly incorporated herein by reference.

FIELD

Provided herein are synergistic herbicidal compositions comprising (a) fluoroxypyr or a salt or ester thereof and (b) flumetsulam or a salt thereof. Also provided herein are methods of controlling undesirable vegetation comprising applying (a) fluoroxypyr or a salt or ester thereof and (b) flumetsulam or a salt thereof.

BACKGROUND

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use. However, there remains a need for additional compositions and methods that are effective in controlling undesirable vegetation.

SUMMARY

Provided herein are synergistic herbicidal compositions which unexpectedly provide increased control of undesirable vegetation comprising an herbicidally effective amount of (a) fluoroxypyr or an agriculturally acceptable salt or ester thereof and (b) flumetsulam or an agriculturally acceptable salt thereof. The compositions may also contain an agriculturally acceptable adjuvant or carrier.

Provided herein are also methods of controlling undesirable vegetation comprising applying (a) fluoroxypyr or an agriculturally acceptable salt or ester thereof and (b) flumetsulam or an agriculturally acceptable salt thereof.

In some embodiments, the compositions or methods described herein provide synergistic weed control. In some embodiments, the compositions or methods described herein provide safening from crop injury. In some embodiments, the compositions or methods described herein are for foliar applications to a crop, including but not limited to, corn/maize, wheat, barley, soybean, rice, sunflower, canola/oilseed rape, sugarcane, sorghum, oats, rye, and cotton crops.

In some embodiments, the compositions or methods described herein are for use in crops comprising an aad-12 gene (e.g., aad-12 soybean or cotton crops, or other acetolactate synthase (ALS) resistant crops comprising an aad-12 gene, e.g., ALS broadleaf or grass resistant crops comprising an aad-12 gene). See, e.g., U.S. Pat. No. 8,283,522; U.S. Pat. No. 8,460,891; US 2012/0110688; US 2012/0277104; all of which are incorporated herein by reference in their entireties. In some embodiments, the compositions or methods described herein are useful for control of a broad spectrum of broadleaf and ALS resistant broadleaf weeds in crops described herein (e.g., soybean or cotton crops comprising an aad-12 gene, or crops comprising an aad-12 gene that are tolerant to ALS herbicides). In some embodiments, the compositions or methods described herein are useful for weed control in crops that are tolerant to ALS mode-of-action herbicides (e.g., flumetsulam), including but not limited to, crops comprising an aad-12 gene. In some embodiments, the compositions or methods described herein are useful for weed control in crops that are normally tolerant to fluoroxypyr and flumetsulam. In some embodiments, the compositions or methods described herein are useful for weed control in non-crop situations.

In one embodiment, auxinic herbicide-resistance genes may be employed with the plants or crops being treated by a composition or in a method described herein. The plants or crops may be transformed to contain one or more of a family of resistance genes (designated aad) that code for an enzyme, aryloxyalkanoate dioxygenase (AAD), which then inactivates an auxin herbicide in planta. Such herbicide resistance may be conferred by aad-1 (originally from *Sphingobium herbicidovorans*), aad-12 (originally from *Delftia acidovorans*), and aad-13 genes as disclosed in U.S. Pat. No. 7,838,733, U.S. Pat. No. 8,283,522, and U.S. Pat. No. 8,278,505, respectively; these publications are incorporated herein by reference. The aad-12 gene (originally from *Delftia acidovorans*) encodes the aryloxyalkanoate dioxygenase (AAD-12) protein. The trait confers tolerance to 2,4-dichlorophenoxyacetic acid (2,4-D), for example, and to pyridyloxyacetate herbicides. The aad-12 gene, itself, for herbicide tolerance in plants is disclosed in, e.g., U.S. Pat. No. 8,283,522.

DETAILED DESCRIPTION

Definitions

As used herein, unless otherwise specified, fluoroxypyr has the following structure:

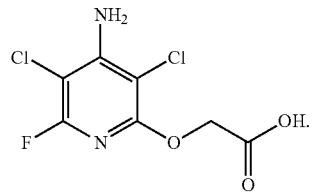 [SMILES: Nc1c(Cl)c(F)nc(OCC(=O)O)c1Cl]

In some embodiments, as used herein, unless otherwise specified, a fluoroxypyr derivative such as fluoroxypyr or a salt or ester thereof has the following structure:

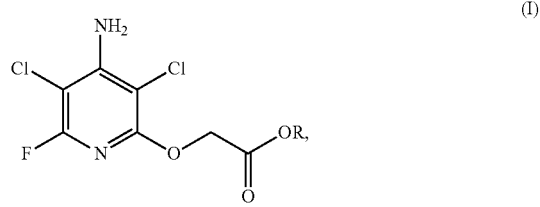

wherein R is hydrogen, a counterion of carboxylic acid, or an optionally substituted alkyl, heteroalkyl, cycloalkyl, heterocyclyl, aryl, or heteroaryl; or a salt thereof. In some embodiments, R is H. In some embodiments, R is a counterion of the carboxylic acid (e.g., a positively charged moiety to form an agriculturally acceptable salt of the carboxylic acid). In some embodiments, R is 1-methylheptyl or meptyl (i.e., —CH(CH$_3$)—(CH$_2$)$_5$—CH$_3$), and the corresponding fluoroxypyr derivative may be referred to as fluoroxypyr-meptyl. In some embodiments, R is 2-butoxy-1-methylethyl or butomethyl (i.e., —CH(CH$_3$)—CH$_2$—O—(CH$_2$)$_3$—CH$_3$), and the corresponding fluoroxypyr derivative may be referred to as fluoroxypyr-butomethyl. Fluoroxypyr can be identified by a chemical name: 4-amino-3,5-dichloro-6-fluoro-2-pyridyloxyacetic acid, or a salt or ester thereof. For example, fluoroxypyr-meptyl can be identified as: (RS)-1-methylheptyl 4-amino-3,5-dichloro-6-fluoro-2-pyridyloxyacetate; and fluoroxypyr-butomethyl can be identified as: (RS)-2-butoxy-1-methylethyl 4-amino-3,5-dichloro-6-fluoro-2-pyridyloxyacetate.

As used herein, unless otherwise specified, flumetsulam has the following structure:

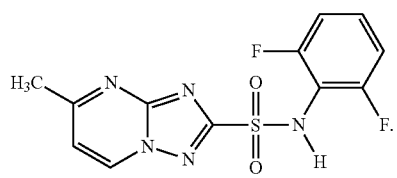

(II)

Flumetsulam can be identified by a chemical name: 2',6'-difluoro-5-methyl[1,2,4]triazolo-[1,5-a]pyrimidine-2-sulfonanilide, or a salt thereof. In some embodiments, as used herein, unless otherwise specified, a flumetsulam derivative includes flumetsulam or a salt thereof.

The herbicidal activities of fluoroxypyr and flumetsulam are exemplified, e.g., in Tomlin, C. D. S., Ed. *The Pesticide Manual: A World Compendium*, 15$^{th}$ ed.; BCPC: Alton, 2009 (hereafter "*The Pesticide Manual*, Fifteenth Edition, 2009"). Exemplary uses of fluoroxypyr include controlling undesirable broadleaf vegetation in multiple non-crop and cropping situations and post-emergence foliar application to broadleaf weeds, e.g., in small grain crops, pastures, grasslands, orchards, corn/maize, sugarcane, and plantation crops. Exemplary uses of flumetsulam include controlling undesirable broadleaf vegetation in multiple non-crop and cropping situations, and pre-planting, pre-emergence or early post-emergence control of broadleaf weeds, e.g., in soybeans, field peas, sugarcane, and corn/maize.

As used herein, herbicide means a compound, i.e., an active ingredient, that kills, controls or otherwise adversely modifies the growth of plants. As used herein, and unless otherwise indicated, herbicidal active ingredient means an ingredient in a composition having substantial herbicidal activities, such as killing, controlling or otherwise adversely modifying undesired growth of plants such as weeds.

As used herein, an herbicidally effective or vegetation controlling amount is an amount of active ingredient which causes an adversely modifying effect to the vegetation, e.g., causing deviations from natural development, killing, effecting regulation, causing desiccation, causing retardation, and the like.

As used herein, controlling undesirable vegetation means preventing, reducing, killing, or otherwise adversely modifying the development of plants and vegetation. Described herein are methods of controlling undesirable vegetation through the application of certain herbicide combinations or compositions. Methods of application include, but are not limited to applications to the vegetation or locus thereof, e.g., application to the area adjacent to the vegetation, as well as pre-emergence, post-emergence, foliar, and in-water applications.

As used herein, plants and vegetation include, but are not limited to, germinant seeds, emerging seedlings, plants emerging from vegetative propagules, immature vegetation, and established vegetation.

As used herein, agriculturally acceptable salts and esters refer to salts and esters that exhibit herbicidal activity or that are or can be converted in plants, water, or soil to the referenced herbicide. Exemplary agriculturally acceptable esters are those that are or can by hydrolyzed, oxidized, metabolized, or otherwise converted, e.g., in plants, water, or soil, to the corresponding carboxylic acid which, depending upon the pH, may be in the dissociated or undissociated form.

Exemplary salts include those derived from alkali or alkaline earth metals and those derived from ammonia and amines. Exemplary cations include sodium, potassium, magnesium, and aminium cations of the formula:

$R^1R^2R^3R^4N^+$ wherein $R^1$, $R^2$, $R^3$ and $R^4$ each independently represents hydrogen or C$_1$-C$_{12}$ alkyl, C$_3$-C$_{12}$ alkenyl, or C$_3$-C$_{12}$ alkynyl, each of which is optionally substituted by one or more hydroxy, C$_1$-C$_4$ alkoxy, C$_1$-C$_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts can be prepared by treatment with a metal hydroxide, such as sodium hydroxide, with an amine, such as ammonia, trimethylamine, diethanolamine, 2-methyl-thiopropylamine, bisallylamine, 2-butoxyethylamine, morpholine, cyclododecylamine, or benzylamine or with a tetraalkylammonium hydroxide, such as tetramethylammonium hydroxide or choline hydroxide.

Exemplary esters include those derived from C$_1$-C$_{12}$ alkyl, C$_3$-C$_{12}$ alkenyl, C$_3$-C$_{12}$ alkynyl or C$_7$-C$_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, C$_1$-C$_4$ alkyl or C$_1$-C$_4$ alkoxy. Esters can be prepared by coupling of the acids with the alcohol using any number of suitable activating agents such as those used for peptide couplings such as dicyclohexylcarbodiimide (DCC) or carbonyl diimidazole (CDI); by reacting the acids with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

As used herein, and unless otherwise indicated, the term "about," when used in connection with amounts, weight ratios, weight percentages, or application rates of ingredients of a composition, means an amount, a weight ratio, a weight percentage, or an application rate that is recognized by those of ordinary skill in the art to provide an herbicidal effect equivalent to that obtained from the specified amount, weight ratio, weight percentage, or application rate is encompassed. Specifically, the term "about" contemplates an amount, a weight ratio, or an application rate within 30%, 25%, 20%, 15%, 10%, or 5% of the specified amount, weight ratio, weight percentage, or application rate.

Compositions and Methods

Provided herein are herbicidal compositions comprising an herbicidally effective amount of (a) fluoroxypyr or an agriculturally acceptable salt or ester thereof and (b) flumetsulam or an agriculturally acceptable salt thereof. In one embodiment, the compositions may also contain an agriculturally acceptable adjuvant or carrier. In some embodiments, the compositions comprise two herbicides selected from (a) fluoroxypyr or an agriculturally acceptable salt or ester thereof and (b) flumetsulam or an agriculturally acceptable salt thereof, each in an herbicidally effective amount. In some embodiments, the compositions comprise no more than two herbicides: (a) fluoroxypyr or an agriculturally acceptable salt or ester thereof and (b) flumetsulam or an agriculturally acceptable salt thereof, as the herbicidal active ingredients of the compositions, each in an herbicidally effective amount. In some embodiments, the compositions comprise an herbicidally effective amount of (a) fluoroxypyr or an agriculturally acceptable salt or ester thereof and (b) flumetsulam or an agriculturally acceptable salt thereof as the herbicidal active ingredients of the compositions. In one embodiment, the compositions may also contain one or more pesticide active ingredients, plant growth regulators, or herbicide safeners. The pesticide active ingredients, plant growth regulators and safeners may include one or more of an herbicide, an insecticide, a fungicide, a plant growth regulator, or an herbicide safener. In some embodiments, the herbicidal compositions provided herein comprise an herbicidally effective amount of (a) fluoroxypyr or an agriculturally acceptable salt or ester thereof and (b) flumetsulam or an agriculturally acceptable salt thereof, and do not comprise 2,4-D or a salt or ester thereof. In some embodiments, the herbicidal compositions provided herein comprise an herbicidally effective amount of (a) fluoroxypyr or an agriculturally acceptable salt or ester thereof and (b) flumetsulam or an agriculturally acceptable salt thereof, and do not comprise another synthetic auxin herbicide. In some embodiments, the herbicidal compositions provided herein comprise an herbicidally effective amount of (a) fluoroxypyr or an agriculturally acceptable salt or ester thereof and (b) flumetsulam or an agriculturally acceptable salt thereof, and may contain additionally 2,4-D, dicamba, clopyralid and diflufenzopyr or a salt or ester thereof.

In some embodiments, the herbicidal compositions provided herein consist essentially of an herbicidally effective amount of (a) fluoroxypyr or an agriculturally acceptable salt or ester thereof and (b) flumetsulam or an agriculturally acceptable salt thereof, as the herbicidal active ingredients of the compositions. In one embodiment, the herbicidal compositions provided herein further comprise one or more agriculturally acceptable adjuvant, carrier, safener, insecticide, fungicide, or plant growth regulator. In one embodiment, the herbicidal compositions do not comprise 2,4-D or a salt or ester thereof. In one embodiment, the herbicidal compositions do not comprise another synthetic auxin herbicide.

In some embodiments, the herbicidal compositions provided herein consist of an herbicidally effective amount of (a) fluoroxypyr or an agriculturally acceptable salt or ester thereof and (b) flumetsulam or an agriculturally acceptable salt thereof as the herbicidal active ingredients of the compositions. In one embodiment, the herbicidal compositions provided herein further comprise one or more agriculturally acceptable adjuvant, carrier, safener, insecticide, fungicide, or plant growth regulator. In one embodiment, the herbicidal compositions do not comprise 2,4-D or a salt or ester thereof. In one embodiment, the herbicidal compositions do not comprise another synthetic auxin herbicide.

Provided herein are also methods of controlling undesirable vegetation comprising contacting the vegetation or the locus thereof, i.e., area adjacent to the vegetation, with or applying to the soil or water to prevent the emergence or growth of vegetation, an herbicidally effective amount of fluoroxypyr or an agriculturally acceptable salt or ester thereof and (b) flumetsulam or an agriculturally acceptable salt thereof. In certain embodiments, the methods employ the compositions described herein.

Furthermore, in some embodiments, the combination of fluoroxypyr or an agriculturally acceptable salt or ester thereof and flumetsulam or an agriculturally acceptable salt thereof exhibits synergism, i.e., the herbicidal active ingredients are more effective in combination than when applied individually. Synergism has been defined as "an interaction of two or more factors such that the effect when combined is greater than the predicted effect based on the response of each factor applied separately." Senseman, S., Ed. Herbicide Handbook. 9$^{th}$ ed. Lawrence: Weed Science Society of America, 2007. In certain embodiments, the compositions exhibit synergy as determined by the Colby equation. Colby, S. R. Calculation of the synergistic and antagonistic response of herbicide combinations. *Weeds* 1967, 15, 20-22.

In certain embodiments of the compositions and methods described herein, the carboxylic acid of fluoroxypyr is employed. In certain embodiments, a salt of the carboxylic acid of fluoroxypyr is employed. In certain embodiments, an arylalkyl, alkyl, or heteroalkyl ester of fluoroxypyr is employed. In certain embodiments, a salt of an arylalkyl, alkyl, or heteroalkyl ester of fluoroxypyr is employed. In certain embodiments, a benzyl, substituted benzyl, $C_{1-10}$ alkyl, or $C_{1-10}$ heteroalkyl ester, e.g., butomethyl or meptyl ester or a salt thereof, is employed. In certain embodiments, the butomethyl ester of fluoroxypyr (i.e., fluoroxypyr-butomethyl) is employed. In certain embodiments, the meptyl ester of fluoroxypyr (i.e., fluoroxypyr-meptyl) is employed.

In some embodiments, fluoroxypyr or a salt or ester thereof and flumetsulam or a salt thereof are formulated in one composition, tank-mixed, applied simultaneously, or applied sequentially.

In some embodiments of the methods described herein, fluoroxypyr and flumetsulam or salts or esters thereof are applied simultaneously, including, i.e., in the form of a composition. In some embodiments, the components are applied sequentially, e.g., within 5, 10, 15, or 30 minutes of each other; within 1, 2, 3, 4, 5, 10, 12, 24, 48 hour(s) of each other, or within 1 week of each other.

Herbicidal activity is exhibited by the compounds when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted to promote non-selective or selective herbicidal action. In some embodiments, the compositions described herein are applied as a post-emergence application, pre-emergence application, or in-water application to flooded paddy rice or water bodies (e.g., ponds, lakes and streams), to relatively immature and mature undesirable vegetation to achieve the maximum control of weeds.

In some embodiments, the compositions and methods provided herein are utilized to control weeds in crops, including but not limited to, direct-seeded, water-seeded and transplanted rice, soybean, cotton, sugarcane, wheat, barley, oats, rye, sorghum, corn/maize, rice, sunflower, canola/oilseed rape, pastures, grasslands, rangelands, fallowland, tree and vine orchards, and in non-crops, including but not limited, to turf, aquatics, industrial vegetation management (IVM), fencerows, parking areas, tank farms, storage areas, airports and highway and utility rights-of-way.

In certain embodiments, the compositions and methods provided herein are utilized to control weeds in wheat, barley, corn/maize, soybean, rice, sunflower, canola/oilseed rape, sugarcane, sorghum, oats, rye or cotton. In certain embodiments, the wheat, barley, corn/maize, soybean, rice, sunflower, canola/oilseed rape, sugarcane, sorghum, oats, rye cotton are direct-seeded into soil.

The compositions and methods described herein can be used to control undesirable vegetation in glyphosate-tolerant-, glufosinate-tolerant-, dicamba-tolerant-, phenoxy auxin-tolerant-, pyridyloxy auxin-tolerant-, aryloxyphenoxypropionate-tolerant-, acetyl CoA carboxylase (ACCase) inhibitor-tolerant-, imidazolinone-tolerant-, acetolactate synthase (ALS) inhibitor-tolerant-, 4-hydroxyphenyl-pyruvate-dioxygenase (HPPD) inhibitor-tolerant-, protoporphyrinogen oxidase (PPO) inhibitor-tolerant-, triazine-tolerant-, bromoxynil-tolerant-crops (such as, but not limited to, soybean, cotton, canola/oilseed rape, rice, cereals, corn/maize, turf, etc.), for example, in conjunction with glyphosate, glufosinate, dicamba, phenoxy auxins, pyridyloxy auxins, aryloxyphenoxypropionates, ACCase inhibitors, imidazolinones, ALS inhibitors, HPPD inhibitors, PPO inhibitors, triazines, and bromoxynil. The compositions and methods can be used in controlling undesirable vegetation in crops possessing multiple or stacked traits conferring tolerance to multiple chemistries and/or inhibitors of multiple modes-of-action. In some embodiments, fluoroxypyr or a salt or ester thereof and flumetsulam or a salt thereof are used in combination with herbicides that are selective for the crop being treated and which complement the spectrum of weeds controlled by these compounds at the application rate employed. In some embodiments, the compositions described herein and other complementary herbicides are applied at the same time, either as a combination formulation or as a tank mix.

The compositions and methods provided herein are utilized to control undesirable vegetation. Undesirable vegetation includes, but is not limited to, undesirable vegetation that occurs in rice, cereals, wheat, range and pasture, row crops (e.g., corn/maize, soybean, cotton, canola/oilseed rape), turf, trees, vines, and ornamental species, aquatic or non-crop settings (e.g., rights-of-way, IVM).

In some embodiments, the methods provided herein are utilized to control undesirable vegetation in rice. In certain embodiments, the undesirable vegetation is *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) LINK (junglerice, ECHCO), *Echinochloa oryzoides* (Ard.) Fritsch (early watergrass, ECHOR), *Echinochloa oryzicola* (Vasinger) Vasinger (late watergrass, ECHPH), *Ischaemum rugosum* Salisb. (saramollagrass, ISCRU), *Leptochloa chinensis* (L.) Nees (Chinese sprangletop, LEFCH), *Leptochloa fascicularis* (Lam.) Gray (bearded sprangletop, LEFFA), *Leptochloa panicoides* (Presl.) Hitchc. (Amazon sprangletop, LEFPA), *Panicum dichotomiflorum* (L.) Michx. (fall *panicum*, PANDI), *Paspalum dilatatum* Poir. (dallisgrass, PASDI), *Cyperus difformis* L. (smallflower flat-sedge, CYPDI), *Cyperus esculentus* L. (yellow nutsedge, CYPES), *Cyperus iria* L. (rice flatsedge, CYPIR), *Cyperus rotundus* L. (purple nutsedge, CYPRO), *Eleocharis* species (ELOSS), *Fimbristylis miliacea* (L.) Vahl (globe fringerush, FIMMI), *Schoenoplectus juncoides* Roxb. (Japanese bulrush, SPCJU), *Schoenoplectus maritimus* L. (sea clubrush, SCPMA), *Schoenoplectus mucronatus* L. (ricefield bulrush, SCPMU), *Aeschynomene* species, (jointvetch, AESSS), *Alternanthera philoxeroides* (Mart.) Griseb. (alligatorweed, ALRPH), *Alisma plantago*-aquatica L. (common waterplantain, ALSPA), *Amaranthus* species, (pigweeds and amaranths, AMASS), *Ammannia coccinea* Rottb. (redstem, AMMCO), *Eclipta alba* (L.) Hassk. (American false daisy, ECLAL), *Heteranthera limosa* (SW.) Willd./Vahl (duck-salad, HETLI), *Heteranthera reniformis* R. & P. (roundleaf mudplantain, HETRE), *Ipomoea hederacea* (L.) Jacq. (ivyleaf morningglory, IPOHE), *Lindernia dubia* (L.) Pennell (low false pimpernel, LIDDU), *Monochoria korsakowii* Regel & Maack (monochoria, MOOKA), *Monochoria vaginalis* (Burm. F.) C. Presl ex Kuhth, (monochoria, MOOVA), *Murdannia nudiflora* (L.) Brenan (doveweed, MUDNU), *Polygonum pensylvanicum* L., (Pennsylvania smartweed, POLPY), *Polygonum persicaria* L. (ladysthumb, POLPE), *Polygonum hydropiperoides* Michx. (POLHP, mild smartweed), *Rotala indica* (Willd.) Koehne (Indian toothcup, ROTIN), *Sagittaria* species, (arrowhead, SAGSS), *Sesbania exaltata* (Raf.) Cory/Rydb. Ex Hill (hemp sesbania, SEBEX), or *Sphenoclea zeylanica* Gaertn. (gooseweed, SPDZE).

In some embodiments, the methods provided herein are utilized to control undesirable vegetation in cereals and wheat. In certain embodiments, the undesirable vegetation is *Alopecurus myosuroides* Huds. (blackgrass, ALOMY), Apera spica-venti (L.) Beauv. (windgrass, APESV), *Avena fatua* L. (wild oat, AVEFA), *Bromus tectorum* L. (downy brome, BROTE), *Lolium multiflorum* Lam. (Italian ryegrass, LOLMU), *Phalaris minor* Retz. (littleseed canarygrass, PHAMI), *Poa annua* L. (annual bluegrass, POANN), *Setaria pumila* (Poir.) Roemer & J. A. Schultes (yellow foxtail, SETLU), *Setaria viridis* (L.) Beauv. (green foxtail, SETVI), *Cirsium arvense* (L.) Scop. (Canada thistle, CIRAR), *Galium aparine* L. (catchweed bedstraw, GALAP), *Kochia scoparia* (L.) Schrad. (kochia, KCHSC), *Lamium purpureum* L. (purple deadnettle, LAMPU), *Matricaria recutita* L. (wild chamomile, MATCH), *Matricaria matricarioides* (Less.) Porter (pineappleweed, MATMT), *Papaver rhoeas* L. (common poppy, PAPRH), *Polygonum convolvulus* L. (wild buckwheat, POLCO), *Salsola tragus* L. (Russian thistle, SASKR), *Stellaria media* (L.) Vill. (common chickweed, STEME), *Veronica persica* Poir. (Persian speedwell, VERPE), *Viola arvensis* Murr. (field violet, VIOAR), or *Viola tricolor* L. (wild violet, VIOTR).

In some embodiments, the methods provided herein are utilized to control undesirable vegetation in range and pasture. In certain embodiments, the undesirable vegetation is *Ambrosia artemisiifolia* L. (common ragweed, AMBEL), *Cassia obtusifolia* (sickle pod, CASOB), *Centaurea maculosa* auct. non Lam. (spotted knapweed, CENMA), *Cirsium arvense* (L.) Scop. (Canada thistle, CIRAR), *Convolvulus arvensis* L. (field bindweed, CONAR), *Euphorbia esula* L. (leafy spurge, EPHES), *Lactuca serriola* L./Torn. (prickly lettuce, LACSE), *Plantago lanceolata* L. (buckhorn plantain, PLALA), *Rumex obtusifolius* L. (broadleaf dock, RUMOB), *Sida spinosa* L. (prickly sida, SIDSP), *Sinapis arvensis* L. (wild mustard, SINAR), *Sonchus arvensis* L. (perennial sowthistle, SONAR), *Solidago* species (goldenrod, SOOSS), *Taraxacum officinale* G. H. Weber ex Wiggers (dandelion, TAROF), *Trifolium repens* L. (white clover, TRFRE), or *Urtica dioica* L. (common nettle, URTDI).

In some embodiments, the methods provided herein are utilized to control undesirable vegetation found in row crops (including but not limited to, soybean, cotton, sunflower, canola/oilseed rape and corn/maize), vegetable crops, plantation crops and tree and vine crops. In certain embodiments, the undesirable vegetation is *Alopecurus myosuroides* Huds. (blackgrass, ALOMY), *Avena fatua* L. (wild oat, AVEFA), *Brachiaria platyphylla* (Groseb.) Nash (broadleaf signalgrass, BRAPP), *Digitaria sanguinalis* (L.) Scop. (large crabgrass, DIGSA), *Echinochloa crus-galli* (L.) P. Beauv. (barnyardgrass, ECHCG), *Echinochloa colonum* (L.) Link (junglerice, ECHCO), *Lolium multiflorum* Lam. (Italian ryegrass, LOLMU), *Panicum dichotomiflorum* Michx. (fall *panicum*, PANDI), *Panicum miliaceum* L. (wild-proso millet, PANMI), *Setaria faberi* Herrm. (giant foxtail, SETFA), *Setaria viridis* (L.) Beauv. (green foxtail, SETVI), *Sorghum halepense* (L.) Pers. (Johnsongrass, SORHA), *Sorghum bicolor* (L.) *Moench* ssp. *Arundinaceum* (shattercane, SORVU), *Cyperus esculentus* L. (yellow nutsedge, CYPES), *Cyperus rotundus* L. (purple nutsedge, CYPRO), *Abutilon theophrasti* Medik. (velvetleaf, ABUTH), *Amaranthus* species (pigweeds and amaranths, AMASS), *Ambrosia artemisiifolia* L. (common ragweed, AMBEL), *Ambrosia psilostachya* DC. (western ragweed, AMBPS), *Ambrosia trifida* L. (giant ragweed, AMBTR), *Asclepias syriaca* L. (common milkweed, ASCSY), *Chenopodium album* L. (common lambsquarters, CHEAL), *Cirsium arvense* (L.) Scop. (Canada thistle, CIRAR), *Commelina benghalensis* L. (tropical spiderwort, COMBE), *Datura stramonium* L. (jimsonweed, DATST), *Daucus carona* L. (wild carrot, DAUCA), *Euphorbia heterophylla* L. (wild poinsettia, EPHHL), *Erigeron bonariensis* L. (hairy fleabane, ERIBO), *Erigeron canadensis* L. (Canadian fleabane, ERICA), *Helianthus annuus* L. (common sunflower, HELAN), *Jacquemontia tamnifolia* (L.) Griseb. (smallflower morningglory, IAQTA), *Ipomoea hederacea* (L.) Jacq. (ivyleaf morningglory, IPOHE), *Ipomoea lacunosa* L. (white morningglory, IPOLA), *Lactuca serriola* L./Torn. (prickly lettuce, LACSE), *Portulaca oleracea* L. (common purslane, POROL), *Sida spinosa* L. (prickly *sida*, SIDSP), *Sinapis arvensis* L. (wild mustard, SINAR), *Solanum ptychanthum* Dunal (eastern black nightshade, SOLPT), or *Xanthium strumarium* L. (common cocklebur, XANST).

In some embodiments, the compositions and methods provided herein are utilized to control undesirable vegetation of grass, broadleaf and sedge weeds, and the like. In certain embodiments, the compositions and methods provided herein are utilized to control undesirable vegetation of, e.g., *Amaranthus, Chenopodium, Ipomoea, Kochia, Polygonum, Rumex*, or *Salsola*. In certain embodiments, the compositions and methods provided herein are utilized to control undesirable vegetation of, e.g., redroot pigweed (*Amaranthus retroflexus* L., AMARE), pigweed species (*Amaranthus* sp., AMASS), common lambsquarters (*Chenopodium album* L., CHEAL), nettleleaf goosefoot (*Chenopodium murale* L., CHEMU), pitted morningglory (*Ipomoea lacunosa* L., IPOLA), kochia (*Kochia scoparia* (L.) Schrad., KCHSC), wild buckwheat (*Polygonum convolvulus* L., POLCO), curly dock (*Rumex crispus* L., RUMCR), or Russian thistle (*Salsola iberica* Sennen & Pau, SASKR). In some embodiments, the combination of fluoroxypyr or an agriculturally acceptable ester or salt thereof and flumetsulam or an agriculturally acceptable salt thereof is used to control redroot pigweed (*Amaranthus retroflexus* L., AMARE), pigweed species (*Amaranthus* sp., AMASS), common lambsquarters (*Chenopodium album* L., CHEAL), nettleleaf goosefoot (*Chenopodium murale* L., CHEMU), pitted morningglory (*Ipomoea lacunosa* L., IPOLA), kochia (*Kochia scoparia* (L.) Schrad., KCHSC), wild buckwheat (*Polygonum convolvulus* L., POLCO), curly dock (*Rumex crispus* L., RUMCR), or Russian thistle (*Salsola iberica* Sennen & Pau, SASKR).

Fluoroxypyr or an agriculturally acceptable salt or ester thereof and flumetsulam or an agriculturally acceptable salt thereof may be used to control herbicide-resistant or -tolerant weeds. The methods employing the combination of fluoroxypyr or an agriculturally acceptable salt or ester thereof and flumetsulam or an agriculturally acceptable salt thereof, or the compositions described herein may also be employed to control herbicide-resistant or -tolerant weeds. Exemplary resistant or tolerant weeds include, but are not limited to, biotypes resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action such as quinclorac, and unclassified herbicides such as arylaminopropionic acids, difenzoquat, endothall, and organoarsenicals. Exemplary resistant or tolerant weeds include, but are not limited to, biotypes with resistance or tolerance to multiple herbicides, multiple chemical classes, and multiple herbicide modes-of-action.

In certain embodiments of the compositions and methods described herein, fluoroxypyr or a salt or ester thereof is used in combination with flumetsulam or a salt thereof at certain weight ratios. In one embodiment, the weight ratios may be calculated based on the acid equivalent weight of fluoroxypyr or a salt or ester thereof (grams acid equivalent or g ae; i.e., for a salt or ester of fluoroxypyr, the molar equivalent weight of fluoroxypyr acid is used) and the equivalent weight of flumetsulam (grams active ingredient or g ai; i.e., for a salt of flumetsulam, the molar equivalent weight of flumetsulam is used) in the compositions. In some embodiments, the weight ratio of fluoroxypyr or a salt or ester thereof to flumetsulam or a salt thereof is within the range of from about 1:100 to about 150:1. In some embodiments, the weight ratio of fluoroxypyr or a salt or ester thereof to flumetsulam or a salt thereof is within the range of from about 1:10 to about 100:1. In some embodiments, the weight ratio of fluoroxypyr or a salt or ester thereof to flumetsulam or a salt thereof is within the range of from about 1:5 to about 50:1. In some embodiments, the weight ratio of fluoroxypyr or a salt or ester thereof to flumetsulam or a salt thereof is within the range of from about 1:2.5 to about 112:1. In some embodiments, the weight ratio of fluoroxypyr or a salt or ester thereof to flumetsulam or a salt thereof is within the range of from about 1:2.5 to about 12:1. In some embodiments, the weight ratio of fluoroxypyr or a salt or ester thereof to flumetsulam or a salt thereof is within the range of from about 100:1 to about 1:50. In some embodiments, the weight ratio of fluoroxypyr or a salt or ester thereof to flumetsulam or a salt thereof is within the range of from about 50:1 to about 1:25. In some embodiments, the weight ratio of fluoroxypyr or a salt or ester thereof to flumetsulam or a salt thereof is within the range of from about 20:1 to about 1:10. In some embodiments, the weight ratio of fluoroxypyr or a salt or ester thereof to flumetsulam or a salt thereof is within the range of from about 1:2.5 to about 3:1. In some embodiments, the weight ratio of fluoroxypyr or a salt or ester thereof to flumetsulam or a salt thereof is within the range of from about 1:2 to about 12:1. In some embodiments, the weight ratio of fluoroxypyr or a salt or ester thereof to flumetsulam or a salt thereof is within the range of from about 1:1 to about 50:1. In some embodiments, the weight ratio of fluoroxypyr or a salt or ester thereof to flumetsulam or a salt thereof is within the range of from about 1:1 to about 40:1. In some embodiments, the weight ratio of fluoroxypyr or a salt or ester thereof to flumetsulam or a salt thereof is within the range of from about 1:1 to about 30:1. In some embodiments, the weight ratio of fluoroxypyr or a salt or ester thereof to flumetsulam or a salt thereof is within the range of from about 1:1 to about 20:1. In some embodiments, the weight ratio of fluoroxypyr or a salt or ester thereof to flumetsulam or a salt thereof is within the range of from about 1:1 to about 10:1. In some embodiments, the weight ratio of fluoroxypyr or a salt or ester thereof to flumetsulam or a salt thereof is within the range of from about 1:1 to about 8:1. In some embodiments, the weight ratio of fluoroxypyr or a salt or ester thereof to flumetsulam or a salt thereof is within the range of from about 1:1 to about 6:1. In some embodiments, the weight ratio of fluoroxypyr or a salt or ester thereof to flumetsulam or a salt thereof is within the range of from about 1:1 to about 5:1. In some embodiments, the weight ratio of fluoroxypyr or a salt or ester thereof to flumetsulam or a salt thereof is within the range of from about 1:1 to about 4:1. In some embodiments, the weight ratio of fluoroxypyr or a salt or ester thereof to flumetsulam or a salt thereof is within the range of from about 1:1 to about 3:1. In some embodiments, the weight ratio of fluoroxypyr or a salt or ester thereof to flumetsulam or a salt thereof is within the range of from about 1:1 to about 2:1. In some embodiments, the weight ratio of fluoroxypyr or a salt or ester thereof to flumetsulam or a salt thereof is within the range of from about 12:1 to about 8:1. In some embodiments, the weight ratio of fluoroxypyr or a salt or ester thereof to flumetsulam or a salt thereof is within the range of from about 12:1 to about 6:1. In some embodiments, the weight ratio of fluoroxypyr or a salt or ester thereof to flumetsulam or a salt thereof is within the range of from about 12:1 to about 5:1. In some embodiments, the weight ratio of fluoroxypyr or a salt or ester thereof to flumetsulam or a salt thereof is within the range of from about 12:1 to about 4:1. In some embodiments, the weight ratio of fluoroxypyr or a salt or ester thereof to flumetsulam or a salt thereof is within the range of from about 1:1 to about 20:1. In some embodiments, the weight ratio of fluoroxypyr or a salt or ester thereof to flumetsulam or a salt thereof is within the range of from about 1:1 to about 30:1. In some embodiments, the weight ratio of fluoroxypyr or a salt or ester thereof to flumetsulam or a salt thereof is within the range of from about 1:2 to about 20:1. In some embodiments, the weight ratio of fluoroxypyr or a salt or ester thereof to flumetsulam or a salt thereof is within the range of from about 1:2 to about 10:1. In certain embodiments, the weight ratio of fluoroxypyr or a salt or ester thereof to flumetsulam or a salt thereof is within the range of from about 1:2 to about 8:1. In certain embodiments, the weight ratio of fluoroxypyr or a salt or ester thereof to flumetsulam or a salt thereof is within the range of from about 1:2 to about 7:1. In certain embodiments, the weight ratio of fluoroxypyr or a salt or ester thereof to flumetsulam or a salt thereof is within the range of from about 1:2 to about 6:1. In certain embodiments, the weight ratio of fluoroxypyr or a salt or ester thereof to flumetsulam or a salt thereof is within the range of from about 1:2 to about 5:1. In certain embodiments, the weight ratio of fluoroxypyr or a salt or ester thereof to flumetsulam or a salt thereof is within the range of from about 1:2 to about 4:1. In certain embodiments, the weight ratio of fluoroxypyr or a salt or ester thereof to flumetsulam or a salt thereof is within the range of from about 1:2 to about 3:1. In certain embodiments, the weight ratio of fluoroxypyr or a salt or ester thereof to flumetsulam or a salt thereof is within the range of from about 1:2 to about 2:1. In certain embodiments, the weight ratio of fluoroxypyr or a salt or ester thereof to flumetsulam or a salt thereof is within the range of from about 1:1.2 to about 8:1. In certain embodiments, the weight ratio of fluoroxypyr or a salt or ester thereof to flumetsulam or a salt thereof is within the range of from about 1:1.2 to about 6:1. In certain embodiments, the weight ratio of fluoroxypyr or a salt or ester thereof to flumetsulam or a salt thereof is within the range of from about 1:1.2 to about 4:1. In certain embodiments, the weight ratio of fluoroxypyr or a salt or ester thereof to flumetsulam or a salt thereof is within the range of from about 1:1.2 to about 3:1. In certain embodiments, the weight ratio of fluoroxypyr or a salt or ester thereof to flumetsulam or a salt thereof is within the range of from about 1:1.2 to about 2:1. In certain embodiments, the weight ratio of fluoroxypyr or a salt or ester thereof to flumetsulam or a salt thereof is about 1:10, about 1:8, about 1:6, about 1:5, about 1:4, about 1:3, about 1:2, about 1:1.5, about 1:1.2, about 1:1, about 1.1:1, about 1.2:1, about 1.25:1, about 1.3:1, about 1.4:1, about 1.5:1, about 1.6:1, about 1.8:1, about 2:1, about 2.5:1, about 3:1, about 3.5:1, about 4:1, about 4.5:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 50:1, about 60:1, about 70:1, about 80:1, about 90:1, about 100:1, about 120:1, about 130:1, about 140:1 or about 150:1.

In certain embodiments, the compositions provided herein comprise (a) fluoroxypyr as an acid or meptyl ester thereof or a salt thereof and (b) flumetsulam. In one embodiment, the composition comprises fluoroxypyr-meptyl and flumetsulam, wherein the weight ratio of fluoroxypyr-meptyl (e.g., calculated based on acid equivalent weight, g ae) to flumetsulam (e.g., calculated based on weight of flumetsulam, g ai) is about 1:100 to about 150:1, about 1:10 to about 100:1, about 1:5 to about 50:1, about 1:2.5 to about 112:1, about 1:2.5 to about 12:1, about 1:2 to about 12:1, about 1:1 to about 50:1, about 1:1 to about 40:1, about 1:1 to about 30:1, about 1:1 to about 20:1, about 1:1 to about 10:1, about 1:1 to about 8:1, about 1:1 to about 6:1, about 1:1 to about 5:1, about 1:1 to about 4:1, about 2:1 to about 4:1, about 2:1 to about 5:1, about 2:1 to about 6:1, about 1:1 to about 3:1, about 1:1 to about 2:1, about 1:2 to about 20:1, about 1:2 to about 15:1, about 1:2 to about 13:1, about 1:2 to about 10:1, about 1:2 to about 8:1, about 1:2 to about 7:1, about 1:2 to about 6:1, about 1:2 to about 5:1, about 1:2 to about 4:1, about 1:2 to about 3:1, about 1:2 to about 2:1, or about 1:1.2 to about 8:1. In one embodiment, the composition comprises fluoroxypyr-meptyl and flumetsulam, wherein the weight ratio of fluoroxypyr-meptyl (i.e., calculated based on acid equivalent weight, g ae) to flumetsulam (i.e., calculated based on weight of flumetsulam, g ai) is about 1:10, about 1:8, about 1:6, about 1:5, about 1:4, about 1:3, about 1:2, about 1:1.5, about 1:1.2, about 1:1, about 1.1:1, about 1.2:1, about 1.25:1, about 1.3:1, about 1.4:1, about 1.5:1, about 1.6:1, about 1.8:1, about 2:1, about 2.5:1, about 3:1, about 3.5:1, about 4:1, about 4.5:1, about 5:1, about 6:1, about 7:1, about 8:1, about 9:1, about 10:1, about 12:1, about 14:1, about 15:1, about 16:1, about 18:1, about 20:1, about 25:1, about 30:1, about 35:1, about 40:1, about 50:1, about 60:1, about 70:1, about 80:1, about 90:1, about 100:1, about 120:1, about 130:1, about 140:1 or about 150:1.

With respect to the methods, in certain embodiments, the methods comprise contacting the undesirable vegetation or locus thereof or applying to the soil or water to prevent the emergence or growth of vegetation a composition described herein. In some embodiments, the composition is applied at an application rate of from about 10 grams acid equivalent per hectare (g ae/ha) to about 635 g ae/ha based on the total amount of active ingredients in the composition. In certain embodiments, the composition is applied at an application rate of from about 35 g ae/ha to about 635 g ae/ha based on the total amount of active ingredients in the composition. In certain embodiments, the composition is applied at an application rate of from about 35 g ae/ha to about 400 g ae/ha based on the total amount of active ingredients in the composition. In certain embodiments, the composition is applied at an application rate of from about 35 g ae/ha to about 200 g ae/ha based on the total amount of active ingredients in the composition. In certain embodiments, the composition is applied at an application rate of from about 45 g ae/ha to about 170 g ae/ha based on the total amount of active ingredients in the composition. In some embodiments, the composition is applied at an application rate of from about 45 grams acid equivalent per hectare (g ae/ha) to about 200 g ae/ha based on the total amount of active ingredients in the composition. In certain embodiments, the composition is applied at an application rate of from about 45 g ae/ha to about 300 g ae/ha based on the total amount of active ingredients in the composition. In certain embodiments, the composition is applied at an application rate of from about 45 g ae/ha to about 400 g ae/ha based on the total amount of active ingredients in the composition. In certain embodiments, the composition is applied at an application rate of from about 40 g ae/ha to about 180 g ae/ha based on the total amount of active ingredients in the composition. In certain embodiments, the composition is applied at an application rate of from about 30 g ae/ha to about 180 g ae/ha based on the total amount of active ingredients in the composition.

In some embodiments, the methods comprise contacting the undesirable vegetation or locus thereof or applying to the soil or water to prevent the emergence or growth of vegetation with fluoroxypyr or a salt or ester thereof and flumetsulam or a salt thereof, e.g., sequentially or simultaneously. In some embodiments, flumetsulam or a salt thereof is applied at a rate of from about 5 g ai/ha to about 75 g ai/ha and fluoroxypyr or a salt or ester thereof is applied at a rate of from about 30 g ae/ha to about 560 g ae/ha. In some embodiments, flumetsulam or a salt thereof is applied at a rate of from about 5 g ai/ha to about 60 g ai/ha and fluoroxypyr or a salt or ester thereof is applied at a rate of from about 35 g ae/ha to about 120 g ae/ha. In some embodiments, flumetsulam or a salt thereof is applied at a rate of from about 9 g ai/ha to about 60 g ai/ha and fluoroxypyr or a salt or ester thereof is applied at a rate of from about 35 g ae/ha to about 110 g ae/ha. In some embodiments, flumetsulam or a salt thereof is applied at a rate of from about 9 g ai/ha to about 60 g ai/ha and fluoroxypyr or a salt or ester thereof is applied at a rate of from about 30 g ae/ha to about 120 g ae/ha. In some embodiments, flumetsulam or a salt thereof is applied at a rate of from about 18 g ai/ha to about 60 g ai/ha and fluoroxypyr or a salt or ester thereof is applied at a rate of from about 35 g ae/ha to about 110 g ae/ha.

In certain embodiments, the methods utilize fluoroxypyr or a salt or ester thereof (i.e., fluoroxypyr-meptyl) and flumetsulam or a salt thereof. In one embodiment, the methods utilize fluoroxypyr-meptyl and flumetsulam, wherein fluoroxypyr-meptyl is applied at a rate of from about 30 g ae/ha to about 120 g ae/ha, and flumetsulam is applied at a rate of from about 9 g ai/ha to about 60 g ai/ha. In one embodiment, the methods utilize fluoroxypyr-meptyl and flumetsulam, wherein fluoroxypyr-meptyl is applied at a rate of from about 35 g ae/ha to about 110 g ae/ha, and flumetsulam is applied at a rate of from about 18 g ai/ha to about 60 g ai/ha. In one embodiment, the methods utilize fluoroxypyr-meptyl and flumetsulam, wherein fluoroxypyr-meptyl is applied at a rate of from about 35 g ae/ha to about 110 g ae/ha, and flumetsulam is applied at a rate of from about 9 g ai/ha to about 60 g ai/ha.

In certain embodiments, the methods and compositions utilizing fluoroxypyr or a salt or ester thereof in combination with flumetsulam or a salt thereof are used to control AMARE, AMASS, CHEAL, CHEMU, IPOLA, KCHSC, POLCO, RUMCR, or SASKR.

In certain embodiments, the methods and compositions utilizing fluoroxypyr or a salt or ester thereof in combination with flumetsulam or a salt thereof are used to control *Amaranthus*, *Chenopodium*, *Ipomoea*, *Kochia*, *Polygonum*, *Rumex*, or *Salsola*.

The components of the mixtures described herein can be applied either separately or as part of a multipart herbicidal system.

The compositions described herein can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. In one embodiment, some of the herbicides that can be employed in conjunction with the compositions and methods described herein include, but are not limited to: 4-CPA, 4-CPB, 4-CPP, 2,4-D, 2,4-D choline salt, 2,4-D esters and amines, 2,4-DB, 3,4-DA, 3,4-DB, 2,4-DEB, 2,4-DEP, 3,4-DP, 2,3,6-TBA, 2,4,5-T, 2,4,5-TB, acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop-methyl, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenquinotrione, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, flurtamone, fluthiacet, fomesafen, foramsulfuron, fosamine, fumiclorac, furyloxyfen, glufosinate, glufosinate-ammonium, glufosinate-P-ammonium, glyphosate, halauxifen, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iodosulfuron-ethyl-sodium, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, metsulfuron-methyl, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, pronamide, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen-ethyl, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac-sodium, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thifensulfurn-methyl, thiobencarb, tiafenacil, tiocarbazil, tioclorim, topramezone, tralkoxydim, triafamone, tri-allate, triasulfuron, triaziflam, tribenuron, tribenuron-methyl, tricamba, triclopyr choline salt, triclopyr esters and salts, tridiphane, trietazine, trifloxysulfuron, trifluralin, triflusulfuron, trifop, trifopsime, trihydroxytriazine, trimeturon, tripropindan, tritac, tritosulfuron, vernolate, xylachlor, benzyl 4-amino-3-chloro-5-fluoro-6-(4-chloro-2-fluoro-3-methoxyphenyl)pyridine-2-carboxylate and salts, esters, optically active isomers and mixtures thereof.

In some embodiments, 2,4-D, 2,4-D choline salt, or a 2,4-D ester or salt is not employed in conjunction with the compositions and methods described herein.

In some embodiments, the compositions described herein are employed in combination with one or more herbicide safeners, such as AD-67 (MON 4660), benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, jiecaowan, jiecaoxi, mefenpyr-diethyl, mephenate, naphthalic anhydride (NA), oxabetrinil, 829148 and N-phenyl-sulfonylbenzoic acid amides, to enhance their selectivity. In some embodiments, the safeners are employed in rice, cereal, or corn/maize settings. In some embodiments, the safener is cloquintocet or an ester or salt thereof. In certain embodiments, cloquintocet is utilized to antagonize harmful effects of the compositions on rice and cereals. In some embodiments, the safener is cloquintocet (mexyl).

In some embodiments, compositions provided herein further comprise at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions. They can also be provided as a pre-mix or tank mixed.

Suitable agricultural adjuvants and carriers include, but are not limited to, crop oil concentrate; nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include, but are not limited to toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. In certain embodiments, water is the carrier for the dilution of concentrates.

Suitable solid carriers include but are not limited to talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, cellulose, and the like.

In some embodiments, the compositions described herein further comprise one or more surface-active agents. In some embodiments, such surface-active agents are employed in both solid and liquid compositions, and in certain embodiments those designed to be diluted with carrier before application. The surface-active agents can be anionic, cationic or nonionic in character and can be employed as emulsifying agents, wetting agents, suspending agents, or for other purposes. Surfactants which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surface-active agents include, but are not limited to salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, and in certain embodiments, methyl esters.

In some embodiments, these materials, such as vegetable or seed oils and their esters, can be used interchangeably as an agricultural adjuvant, as a liquid carrier or as a surface active agent.

Other exemplary additives for use in the compositions provided herein include but are not limited to compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

In some embodiments, the concentration of the active ingredients in the compositions described herein is from about 0.0005 to 98 percent by weight. In some embodiments, the concentration is from about 0.0006 to 90 percent by weight. In compositions designed to be employed as concentrates, the active ingredients, in certain embodiments, are present in a concentration from about 0.1 to 98 weight percent, and in certain embodiments about 0.5 to 90 weight percent. Such compositions are, in certain embodiments, diluted with an inert carrier, such as water, before application. The diluted compositions usually applied to weeds or the locus of weeds contain, in certain embodiments, about 0.007 to 8 weight percent active ingredient and in certain embodiments contain about 0.01 to 5.0 weight percent.

The present compositions can be applied to weeds or their locus by the use of conventional ground or aerial dusters, sprayers, and granule applicators, by addition to irrigation or paddy water, and by other conventional means known to those skilled in the art.

The described embodiments and following examples are for illustrative purposes and are not intended to limit the scope of the claims. Other modifications, uses, or combinations with respect to the compositions described herein will be apparent to a person of ordinary skill in the art without departing from the spirit and scope of the claimed subject matter.

EXAMPLES

Example I

Evaluation of Post-Emergence Herbicidal Activity of Mixtures of Fluoroxypyr-Meptyl and Flumetsulam in the Field Multiple post-emergence field trials were conducted under field conditions in the United States (Mississippi, South Dakota, and Minnesota) and Mexico. Trial sites were located in commercially grown fields of corn (ZEAMX), spring wheat (TRZAS), and winter wheat (TRZAW), using standard herbicide small plot research methodology. Post-emergence trial plot size varied from 2 to 3 meter (m)×4 to 5 m (width× length) with 4 replicates per treatment. The crops were grown using normal cultural practices for fertilization, seeding, watering, and maintenance to ensure good growth of the crops and the weeds.

All treatments in the post-emergence field trials were applied using a backpack compressed carbon dioxide ($CO_2$) or nitrogen ($N_2$) sprayer with flat fan nozzles calibrated to apply 94 to 250 liters per hectare (L/ha) spray volume at approximately 30-40 pounds per square inch (psi) nozzle pressure. Commercially available products of fluoroxypyr-meptyl (STARANE® 200, 200 grams acid equivalent per liter (g ae/L) and fluoroxypyr-meptyl EC 240 g ae/L) and flumetsulam (75WDG) were mixed in water at appropriate formulated product rates to achieve the desired rates based on a unit area of application (hectare) to achieve the desired rates as shown. All treatments were mixed with crop oil concentrate at 1.25 L/ha or X-77 at 0.25% volume per volume (vol/vol). Treatments were rated at 7 to 45 days after application (DAA) as compared to the untreated control plants. Visual weed control was scored on a scale of 0 to 100 percent where "0" corresponds to no injury and "100" corresponds to complete kill.

All treatment results, both for the single product and mixtures, are an average of 4 replicates. The trial sites had naturally occurring populations of weeds. The weed spectrum included, but was not limited to, AMARE, AMASS, CHEAL, CHEMU, IPOLA, KCHSC, POLCO, RUMCR, and SASKR.

Data were collected for all trials and analyzed using various statistical methods.

Colby's equation was used to determine the herbicidal effects expected from the mixtures (Colby, S. R. Calculation of the synergistic and antagonistic response of herbicide combinations. *Weeds* 1967 15, 20-22). A t-test (alpha=0.05) between Colby predictions and observed combinations was used to test for significant differences indicating synergy or antagonism using replicate data. The results presented in Tables 1-5 were significant according to the described criteria.

The following equation was used to calculate the expected activity of mixtures containing two active ingredients, A and B:

Expected=$A+B-(A \times B/100)$

A=observed efficacy of active ingredient A at the same concentration as used in the mixture;

B=observed efficacy of active ingredient B at the same concentration as used in the mixture.

The compounds tested, application rates employed, plant species tested, and results from in-crop field trials are given in Tables 1-2.

TABLE 1

Synergistic Activity of Foliar-Applied Flumetsulam plus Fluroxypyr-Meptyl when evaluated 7 to 30 Days After Application to Broadleaf Weeds in the Field.

| Weed Bayer Code | Days After Application | Flumetsulam g ai/ha | Flumetsulam % Visual Weed Control | Fluroxypyr-Meptyl g ae/ha | Fluroxypyr-Meptyl % Visual Weed Control | Observed Combined % Visual Weed Control | Colby Predicted % Visual Weed Control |
|---|---|---|---|---|---|---|---|
| AMARE | 13 | 18 | 81 | 110 | 8 | 93 | 82 |
| AMARE | 28 | 35 | 45 | 110 | 13 | 75 | 52 |
| AMARE | 28 | 35 | 45 | 35 | 3 | 70 | 47 |
| AMASS | 7 | 20 | 79 | 75 | 15 | 94 | 82 |
| AMASS | 14 | 20 | 81 | 50 | 21 | 92 | 85 |
| AMASS | 14 | 20 | 81 | 75 | 18 | 97 | 85 |
| CHEAL | 30 | 15 | 31 | 75 | 20 | 55 | 44 |
| CHEAL | 30 | 30 | 35 | 75 | 20 | 60 | 48 |
| CHEAL | 30 | 60 | 40 | 75 | 20 | 64 | 52 |
| CHEMU | 30 | 60 | 69 | 50 | 20 | 79 | 75 |
| CHEMU | 30 | 15 | 57 | 75 | 28 | 85 | 69 |
| CHEMU | 30 | 30 | 66 | 75 | 28 | 88 | 75 |
| CHEMU | 30 | 60 | 69 | 75 | 28 | 93 | 78 |

AMARE = pigweed, redroot (*Amaranthus retroflexus* L.)

AMASS = pigweed species (*Amaranthus* sp.)

CHEAL = lambsquarters, common (*Chenopodium album* L.)

CHEMU = goosefoot, nettleleaf (*Chenopodium murale* L.)

g ae/ha = grams acid equivalent per hectare g ai/ha = grams active ingredient per hectare Observed = Observed % Visual Weed Control in the field Colby Predicted = Expected % Visual Weed Control value as calculated by Colby's equation Days After Application = the number of days from treatment to visual evaluation

TABLE 2

Synergistic Activity of Foliar-Applied Flumetsulam plus Fluroxypyr-Meptyl when evaluated 28 to 45 Days After Application to Broadleaf Weeds in the Field.

| Weed Bayer Code | Days After Application | Flumetsulam g ai/ha | Flumetsulam % Visual Weed Control | Fluroxypyr-Meptyl g ae/ha | Fluroxypyr-Meptyl % Visual Weed Control | Observed Combined % Visual Weed Control | Colby Predicted % Visual Weed Control |
|---|---|---|---|---|---|---|---|
| IPOLA | 28 | 18 | 33 | 70 | 20 | 95 | 47 |
| KCHSC | 28 | 35 | 58 | 35 | 30 | 89 | 71 |
| POLCO | 28 | 18 | 0 | 35 | 38 | 74 | 38 |
| POLCO | 28 | 35 | 0 | 35 | 38 | 71 | 38 |
| POLCO | 28 | 35 | 0 | 70 | 64 | 86 | 64 |
| RUMCR | 45 | 15 | 40 | 75 | 50 | 87 | 70 |
| RUMCR | 45 | 30 | 52 | 75 | 50 | 94 | 76 |

TABLE 2-continued

Synergistic Activity of Foliar-Applied Flumetsulam plus Fluroxypyr-Meptyl when evaluated 28 to 45 Days After Application to Broadleaf Weeds in the Field.

| Weed Bayer Code | Days After Application | Flumetsulam g ai/ha | Flumetsulam % Visual Weed Control | Fluroxypyr-Meptyl g ae/ha | Fluroxypyr-Meptyl % Visual Weed Control | Observed Combined % Visual Weed Control | Colby Predicted % Visual Weed Control |
|---|---|---|---|---|---|---|---|
| RUMCR | 45 | 60 | 70 | 75 | 50 | 96 | 85 |
| SASKR | 29 | 9 | 67 | 35 | 23 | 88 | 74 |

IPOLA = morningglory, pitted (*Ipomoea lacunosa* L.)
KCHSC = kochia (*Kochia scoparia* (L.) Schrad.)
POLCO = buckwheat, wild (*Polygonum convolvulus* L.)
RUMCR = dock, curly (*Rumex crispus* L.)
SASKR = thistle, Russian (*Salsola iberica* Sennen & Pau)
g ae/ha = grams acid equivalent per hectare
g ai/ha = grams active ingredient per hectare
Observed = Observed % Visual Weed Control in the field
Colby Predicted = Expected % Visual Weed Control value as calculated by Colby's equation
Days After Application = the number of days from treatment to visual evaluation Further provided herein are the following embodiments:
1. A synergistic herbicidal composition consisting essentially of an herbicidally effective amount of (a) fluoroxypyr or an agriculturally acceptable salt or ester thereof and (b) flumetsulam or an agriculturally acceptable salt thereof as herbicidal active ingredients of the composition.
2. A synergistic herbicidal composition consisting of an herbicidally effective amount of (a) fluoroxypyr or an agriculturally acceptable salt or ester thereof and (b) flumetsulam or an agriculturally acceptable salt thereof as herbicidal active ingredients of the composition.
3. An herbicidal composition comprising two herbicidal active ingredients selected from (a) fluoroxypyr or an agriculturally acceptable salt or ester thereof and (b) flumetsulam or an agriculturally acceptable salt thereof.
4. The composition of any of embodiments 1-3, wherein (a) is fluoroxypyr-meptyl.
5. The composition of any of embodiments 1-3, wherein (a) is a compound of formula (I), wherein R is H, or an agriculturally acceptable salt thereof:

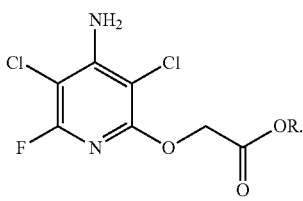

(I)

6. The composition of any of embodiments 1-5, wherein (b) is flumetsulam.
7. The composition of any of embodiments 1-6, further comprising one or more herbicide safeners.
8. The composition of any of embodiments 1-7, further comprising one or more plant growth regulators.
9. The composition of any of embodiments 1-8, further comprising one or more pesticide active ingredients.
10. The composition of any of embodiments 1-8, further comprising one or more insecticides.
11. The composition of any of embodiments 1-8, further comprising one or more fungicides.
12. The composition of any of embodiments 1-11, further comprising one or more agriculturally acceptable adjuvants or carriers.
13. The composition of any of embodiments 1-12, wherein the weight ratio of (a) fluoroxypyr or an agriculturally acceptable salt or ester thereof to (b) flumetsulam or an agriculturally acceptable salt thereof is from about 1:2.5 to about 112:1.
14. The composition of any of embodiments 1-12, wherein the weight ratio of (a) fluoroxypyr or an agriculturally acceptable salt or ester thereof to (b) flumetsulam or an agriculturally acceptable salt thereof is from about 1:2 to about 13:1.
15. The composition of any of embodiments 1-12, wherein the weight ratio of (a) fluoroxypyr or an agriculturally acceptable salt or ester thereof to (b) flumetsulam or an agriculturally acceptable salt thereof is from about 2:1 to about 4:1.
16. The composition of any of embodiments 1-15, which is synergistic as determined by the Colby equation.
17. A method of controlling undesirable vegetation, which comprises contacting the vegetation or the locus thereof with or applying to the soil to prevent the emergence or growth of vegetation, an herbicidal composition comprising an herbicidally effective amount of (a) fluoroxypyr or an agriculturally acceptable salt or ester thereof and (b) flumetsulam or an agriculturally acceptable salt thereof, wherein the undesirable vegetation is controlled in one or more crops comprising an aad-1, aad-12 and aad-13 gene.
18. A method of controlling undesirable vegetation, which comprises contacting the vegetation or the locus thereof with or applying to the soil to prevent the emergence or growth of vegetation, an herbicidal composition comprising an herbicidally effective amount of (a) fluoroxypyr or an agriculturally acceptable salt or ester thereof and (b) flumetsulam or an agriculturally acceptable salt thereof, wherein the undesirable vegetation is controlled in one or more crops comprising an aad-12 gene.
19. The method of embodiment 18, wherein the undesirable vegetation is controlled in wheat, barley, corn/maize, soybean, rice, sunflower, canola/oilseed rape, sugarcane, sorghum, oats, rye or cotton, wherein the wheat, barley, corn/maize, soybean, rice, sunflower, canola/oilseed rape, sugarcane, sorghum, oats, rye or cotton comprises an aad-12 gene.
20. A method of controlling undesirable vegetation, which comprises contacting the vegetation or the locus thereof with or applying to the soil to prevent the emergence or growth of vegetation, the composition of any of embodiments 1-16.
21. The method of embodiment 20, wherein the undesirable vegetation is controlled in soybean, cotton, sugarcane, wheat, barley, oats, rye, sorghum, corn/maize, rice, sunflower, canola/oilseed rape, sugarcane, pastures, grasslands, rangelands, fallowland, turf, tree and vine orchards, industrial vegetation management or rights-of-way.

22. The method of embodiment 20 or embodiment 21, wherein the undesirable vegetation is controlled in one or more crops comprising an aad-12 gene.

23. The method of any of embodiments 17-22, wherein the undesirable vegetation is immature or mature.

24. The method of any of embodiments 17-23, wherein the (a) and (b) of the composition are applied pre-emergently.

25. The method of any of embodiments 17-23, wherein the (a) and (b) of the composition are applied post-emergently.

26. The method of any of embodiments 17-25, wherein the undesirable vegetation is controlled in glyphosate-, glufosinate-, dicamba-, phenoxy auxins-, pyridyloxy auxins-, aryloxyphenoxypropionates-, acetyl CoA carboxylase (ACCase) inhibitors-, imidazolinones-, acetolactate synthase (ALS) inhibitors-, 4-hydroxyphenyl-pyruvate dioxygenase (HPPD) inhibitors-, protoporphyrinogen oxidase (PPO) inhibitors-, triazines-, or bromoxynil-tolerant crop, wherein the tolerant crop optionally comprises an aad-12 gene.

27. The method of embodiment 26, wherein the tolerant crop possesses multiple or stacked traits conferring tolerance to multiple herbicides or multiple modes-of-action.

28. The method of any of embodiments 17-27, wherein the undesirable vegetation comprises an herbicide-resistant or tolerant weed.

29. The method of embodiment 28, wherein the resistant or tolerant weed is a biotype with resistance or tolerance to multiple herbicides, multiple chemical classes, or multiple herbicide modes-of-action.

30. The method of embodiment 28 or embodiment 29, wherein the resistant or tolerant weed is a biotype resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

31. The method of any of embodiments 17-30, wherein (a) is applied at a rate of from about 30 g ae/ha to about 560 g ae/ha and (b) is applied at a rate of from about 5 g ai/ha to about 75 g ai/ha.

32. The method of any of embodiments 17-30, wherein (a) is applied at a rate of from about 35 g ae/ha to about 110 g ae/ha and (b) is applied at a rate of from about 9 g ai/ha to about 60 g ai/ha.

33. The method of any of embodiments 17-32, wherein the undesirable vegetation is *Amaranthus, Chenopodium, Ipomoea, Kochia, Polygonum, Rumex,* or *Salsola.*

34. The method of any of embodiments 17-33, wherein the undesirable vegetation is *Amaranthus retroflexus* L., *Amaranthus* sp., *Chenopodium album* L., *Chenopodium murale* L., *Ipomoea lacunosa* L., *Kochia scoparia* (L.) Schrad., *Polygonum convolvulus* L., *Rumex crispus* L., or *Salsola iberica* Sennen & Pau.

What is claimed is:

1. A synergistic herbicidal composition consisting essentially of an herbicidally effective amount of (a) fluoroxypyr or an agriculturally acceptable salt or ester thereof and (b) flumetsulam or an agriculturally acceptable salt thereof as herbicidal active ingredients of the composition,
wherein (a) and (b) are present in a synergistic amount, and wherein the weight ratio of (a) to (b) is from about 1:1 to 1:10.

2. The composition of claim 1, wherein (a) is fluoroxypyrmeptyl.

3. The composition of claim 1, wherein (a) is fluoroxypyr or an agriculturally acceptable salt thereof.

4. The composition of claim 1, wherein (b) is flumetsulam.

5. The composition of claim 1, further comprising one or more herbicide safeners.

6. The composition of claim 1, further comprising one or more plant growth regulators.

7. The composition of claim 1, further comprising one or more pesticide active ingredients.

8. The composition of claim 1, further comprising one or more insecticides.

9. The composition of claim 1, further comprising one or more fungicides.

10. The composition of claim 1, further comprising one or more agriculturally acceptable adjuvants or carriers.

11. The composition of claim 1, wherein the weight ratio of (a) fluoroxypyr or an agriculturally acceptable salt or ester thereof to (b) flumetsulam or an agriculturally acceptable salt thereof is from about 1:1 to 1:2.

12. The composition of claim 1, wherein the weight ratio of (a) fluoroxypyr or an agriculturally acceptable salt or ester thereof to (b) flumetsulam or an agriculturally acceptable salt thereof is about 1:1.

13. A method of controlling undesirable vegetation, which comprises contacting the vegetation or the locus thereof with or applying to the soil to prevent the emergence or growth of vegetation, the composition of claim 1.

14. The method of claim 13, wherein the undesirable vegetation is controlled in soybean, cotton, sugarcane, wheat, barley, oats, rye, sorghum, corn/maize, rice, sunflower, canola/oilseed rape, sugarcane, pastures, grasslands, rangelands, fallowland, turf, tree and vine orchards, industrial vegetation management or rights-of-way.

15. The method of claim 13, wherein the undesirable vegetation is controlled in one or more crops comprising an aad-12 gene.

16. A synergistic herbicidal composition consisting of an herbicidally effective amount of (a) fluoroxypyr or an agriculturally acceptable salt or ester thereof and (b) flumetsulam or an agriculturally acceptable salt thereof as herbicidal active ingredients of the composition,
wherein (a) and (b) are present in a synergistic amount, and wherein the weight ratio of (a) to (b) is from about 1:1 to 1:10.

17. An herbicidal composition comprising two herbicidal active ingredients selected from (a) fluoroxypyr or an agriculturally acceptable salt or ester thereof and (b) flumetsulam or an agriculturally acceptable salt thereof,
wherein (a) and (b) are present in a synergistic amount, and wherein the weight ratio of (a) to (b) is from about 1:1 to 1:10.

18. A method of controlling undesirable vegetation, which comprises contacting the vegetation or the locus thereof with or applying to the soil to prevent the emergence or growth of vegetation, an herbicidal composition comprising an herbicidally effective amount of (a) fluoroxypyr or an agriculturally acceptable salt or ester thereof and (b) flumetsulam or an agriculturally acceptable salt thereof, wherein the undesirable vegetation is controlled in one or more crops comprising an aad-1, aad-12, or aad-13 gene wherein (a) and (b) are present in a synergistic amount, and wherein the weight ratio of (a) to (b) is from about 1:1 to 1:10.

19. The method of claim 18, wherein the undesirable vegetation is controlled in one or more crops comprising an aad-12 gene.

20. The method of claim 19, wherein the undesirable vegetation is controlled in wheat, barley, corn/maize, soybean, rice, sunflower, canola/oilseed rape, sugarcane, sorghum, oats, rye or cotton, wherein the wheat, barley, corn/maize, soybean, rice, sunflower, canola/oilseed rape, sugarcane, sorghum, oats, rye or cotton comprises an aad-12 gene.

21. The method of claim 19, wherein the undesirable vegetation is immature or mature.

22. The method of claim 19, wherein the (a) and (b) of the composition are applied pre-emergently.

23. The method of claim 19, wherein the (a) and (b) of the composition are applied post-emergently.

24. The method of claim 19, wherein the undesirable vegetation is controlled in glyphosate-, glufosinate-, dicamba-, phenoxy auxins-, pyridyloxy auxins-, aryloxyphenoxypropionates-, acetyl CoA carboxylase (ACCase) inhibitors-, imidazolinones-, acetolactate synthase (ALS) inhibitors-, 4-hydroxyphenyl-pyruvate dioxygenase (HPPD) inhibitors-, protoporphyrinogen oxidase (PPO) inhibitors-, triazines-, or bromoxynil-tolerant crop, wherein the tolerant crop optionally comprises an aad-12 gene.

25. The method of claim 24, wherein the tolerant crop possesses multiple or stacked traits conferring tolerance to multiple herbicides.

26. The method of claim 19, wherein the undesirable vegetation comprises an herbicide-resistant or tolerant weed.

27. The method of claim 26, wherein the resistant or tolerant weed is a biotype with resistance or tolerance to multiple herbicides or multiple herbicide modes-of-action.

28. The method of claim 26, wherein the resistant or tolerant weed is a biotype resistant or tolerant to acetolactate synthase (ALS) inhibitors, photosystem II inhibitors, acetyl CoA carboxylase (ACCase) inhibitors, synthetic auxins, photosystem I inhibitors, 5-enolpyruvylshikimate-3-phosphate (EPSP) synthase inhibitors, microtubule assembly inhibitors, lipid synthesis inhibitors, protoporphyrinogen oxidase (PPO) inhibitors, carotenoid biosynthesis inhibitors, very long chain fatty acid (VLCFA) inhibitors, phytoene desaturase (PDS) inhibitors, glutamine synthetase inhibitors, 4-hydroxyphenyl-pyruvate-dioxygenase (HPPD) inhibitors, mitosis inhibitors, cellulose biosynthesis inhibitors, herbicides with multiple modes-of-action, quinclorac, arylaminopropionic acids, difenzoquat, endothall, or organoarsenicals.

29. The method of claim 19, wherein (a) is applied at a rate of from about 30 g ae/ha to about 560 g ae/ha and (b) is applied at a rate of from about 5 g ai/ha to about 75 g ai/ha.

30. The method of claim 19, wherein (a) is applied at a rate of from about 35 g ae/ha to about 110 g ae/ha and (b) is applied at a rate of from about 9 g ai/ha to about 60 g ai/ha.

31. The method of claim 19, wherein the undesirable vegetation is *Amaranthus, Chenopodium, Ipomoea, Kochia, Polygonum, Rumex*, or *Salsola*.

32. The method of claim 19, wherein the undesirable vegetation is *Amaranthus retroflexus* L., *Amaranthus* sp., *Chenopodium album* L., *Chenopodium murale* L., *Ipomoea lacunosa* L., *Kochia scoparia* (L.) Schrad., *Polygonum convolvulus* L., *Rumex crispus* L., or *Salsola iberica* Sennen & Pau.

* * * * *